United States Patent [19]
von Deyn et al.

[11] Patent Number: 5,846,907
[45] Date of Patent: Dec. 8, 1998

[54] HERBICIDALLY ACTIVE PYRAZOL-4-YLBENZOYL COMPOUNDS

[75] Inventors: Wolfgang von Deyn, Neustadt; Regina Luise Hill, Speyer; Uwe Kardorff, Mannheim; Stefan Engel, Idstein; Martina Otten, Ludwigshafen; Marcus Vossen, Mannheim; Peter Plath, Frankenthal; Harald Rang, Altrip; Albrecht Harreus, Ludwigshafen; Hartmann König, Heidelberg; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 875,664

[22] PCT Filed: Feb. 14, 1996

[86] PCT No.: PCT/EP96/00635

§ 371 Date: Jul. 30, 1997

§ 102(e) Date: Jul. 30, 1997

[87] PCT Pub. No.: WO96/26206

PCT Pub. Date: Aug. 29, 1996

[30] Foreign Application Priority Data

Feb. 24, 1995 [DE] Germany .................. 195 06 572.7

[51] Int. Cl.$^6$ .................. A01N 43/76; A01N 43/80; C07D 261/10; C07D 263/30; C07D 277/22; C07D 307/38; C07D 521/00

[52] U.S. Cl. .................. 504/221; 564/234; 564/242; 564/244; 564/261; 564/263; 564/265; 564/266; 564/270; 564/271; 564/274; 564/283; 564/288; 564/289; 564/290; 564/291; 564/294; 564/295; 544/53; 544/318; 544/335; 546/174; 546/330; 548/128; 548/131; 548/136; 548/141; 548/143; 548/204; 548/214; 548/236; 548/247; 548/267.4; 548/370.1; 548/550; 548/551; 548/364.1; 548/364.7; 548/365.7; 549/38; 549/39; 549/77; 549/450; 549/451; 558/405

[58] Field of Search .................. 548/364.1, 365, 548/7, 128, 131, 136, 141, 143, 204, 214, 236, 247, 267.4, 370.1, 364.7, 365.1, 550, 551; 549/38, 39, 77, 450, 451; 558/405; 504/234, 242, 244, 261, 263, 265, 266, 270, 271, 274, 283, 288, 289, 290, 291, 294, 295; 544/53, 318, 335; 546/174, 330

[56] References Cited

FOREIGN PATENT DOCUMENTS 0282944  9/1988  European Pat. Off. .
0410552  1/1991  European Pat. Off. .

OTHER PUBLICATIONS

King, "Medicinal Chemistry: Principles and Practice", pp. 206 to 209 (1994).

*Primary Examiner*—Floyd D. Higel
*Attorney, Agent, or Firm*—Keil & Weinkauf

[57] ABSTRACT

Pyrazol-4-ylbenzoyl compounds of the formula I

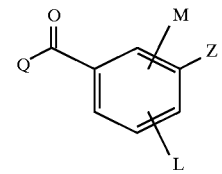

where Z is a 5- or 6-membered heterocyclic saturated or unsaturated radical, Q is a pyrazole ring and L and M are as defined in the specification, their use as herbicidal compounds and to processes for preparing the compounds.

8 Claims, No Drawings

HERBICIDALLY ACTIVE PYRAZOL-4-YLBENZOYL COMPOUNDS

This application is a 371 of PCT/EP96/00635 filed Feb. 14, 1996.

The present invention relates to novel herbicidally active pyrazolylbenzoyl compounds, to processes for the preparation of the pyrazolylbenzoyl compounds, to compositions comprising them, and to the use of these compounds or compositions comprising them for controlling weeds.

Herbicidally active pyrazolylbenzoyl compounds have been disclosed in the literature, for example in EP 352543.

However, the herbicidal properties of the known compounds and their tolerance by crop plants are not entirely satisfactory.

It was an object of the present invention to find novel pyrazolylbenzoyl compounds with improved properties.

We have found that this object is achieved by novel pyrazolylbenzoyl compounds of the formula I

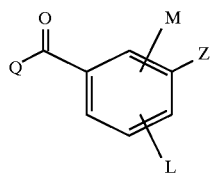

where the substituents are as follows:

L, M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy or are halogen, cyano, nitro, a group $-(Y)_n-S(O)_m R^7$ or a group $-(Y)_n-CO-R^8$ Z is a 5- or 6-membered heterocyclic saturated or unsaturated radical which has one to three hetero atoms selected from the group consisting of oxygen, sulfur and nitrogen and which is unsubstituted or substituted by halogen, cyano, nitro, a group $-CO-R^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, by phenyl which is unsubstituted or substituted by halogen, cyano, nitro, $C_1$–$C_4$-alkyl or $C_1$–$C_4$-haloalkyl, or by an oxo group which may also be present as a hydroxyl group in the tautomeric form, or which forms a bicyclic system together with a fused phenyl ring which is unsubstituted or substituted by halogen, cyano, nitro, $C_1$–$C_4$-alkyl or $C_1$–$C_4$-haloalkyl or with a fused carbocycle or with a fused second heterocycle which is unsubstituted or substituted by halogen, cyano, nitro, $C_1$–$C_4$-alkyl, di-$C_1$–$C_4$-alkylamino, $C_1$–$C_4$-alkoxy, $C_1$–$C_4$-haloalkoxy or $C_1$–$C_4$-haloalkyl, Y is O or $NR^9$, n is zero or 1, m is zero, 1 or 2, $R^7$ is $C_1$–$C_4$-alkyl, $C_1$–$C_4$-haloalkyl or $NR^9 R^{10}$, $R^8$ is $C_1$–$C_4$-alkyl, $C_1$–$C_4$-haloalkyl, $C_1$–$C_4$-alkoxy or $NR^9 R^{10}$, $R^9$ is hydrogen or $C_1$–$C_4$-alkyl, $R^{10}$ is $C_1$–$C_4$-alkyl, Q is a pyrazole ring of the formula II

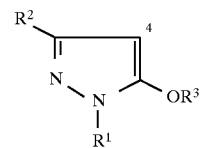

where $R^1$ is $C_1$–$C_4$-alkyl, $R^2$ is hydrogen, $C_1$–$C_4$-alkyl or $C_1$–$C_4$-haloalkyl and $R^3$ is hydrogen, $C_1$–$C_4$-alkylsulfonyl, phenylsulfonyl or alkylphenylsulfonyl and which is linked in the 4-position, and salts of the compounds I which are customary in agriculture.

Compounds of the formula I are obtained by acylating 5-hydroxypyrazoles of the formula IIa with a benzoyl derivative of the formula III (T=Cl) and subjecting the pyrazole ester formed to a rearrangement reaction to give the compounds of the formula Ic.

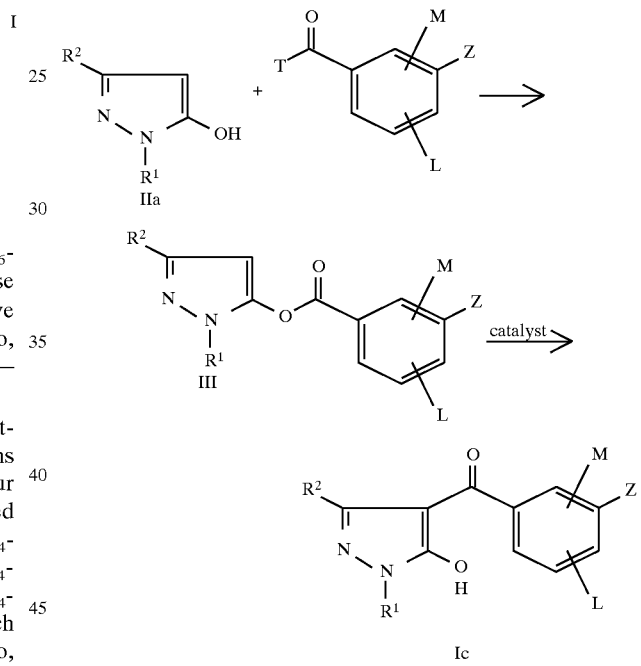

In the abovementioned formulae, T is halogen and L, M and Z are as described at the outset.

The first step of the reaction sequence, namely the acylation, is carried out in a generally known manner, for example by adding a benzoyl derivative of the formula III (T=Cl) to the solution or suspension of a 5-hydroxypyrazole IIa in the presence of an auxiliary base. The reactants and the auxiliary base are expediently employed in approximately equimolar amounts. A slight excess of the auxiliary base, for example 1.2 to 1.5 mol equivalents, based on II, may be advantageous in some cases.

Suitable auxiliary bases are for example tertiary alkylamines, pyridine or alkali metal carbonates, while methylene chloride, diethyl ether, toluene or ethyl acetate can be used as solvents. During the addition of the acid chloride, the reaction mixture is advantageously cooled to 0°–10° C., and the mixture is then stirred at a higher temperature, for example at 25°–50° C., until the reaction has ended.

Work-up is carried out in the customary manner, for example the reaction mixture is poured into water and extracted using methylene chloride. After the organic phase has been dried and the solvent removed, the crude 5-hydroxypyrazole ester can be employed in the rearrangement reaction without further purification. Preparation examples for benzoic esters of 5-hydroxypyrazoles can be found, for example, in EP-A-282 944 or U.S. Pat. No. 4,643,757.

The rearrangement reaction of the 5-hydroxypyrazole esters which gives the compounds of the formula Ic is expediently carried out at temperatures from 20° C. to 40° C. in a solvent and in the presence of an auxiliary base and with the aid of a cyano compound as catalyst. Examples of solvents which can be used are acetonitrile, methylene chloride, 1,2-dichloroethane, ethyl acetate or toluene. The preferred solvent is acetonitrile. Suitable auxiliary bases are tertiary alkylamines, pyridine or alkali metal carbonates, which are employed in an equimolar amount or in up to four-fold excess. The preferred auxiliary base is a two-fold amount of triethylamine. Suitable catalysts are cyanide compounds, such as potassium cyanide or acetone cyanohydrin, for example in an amount of 1 to 50, in particular 5–50, mol percent, based on the 5-hydroxypyrazole ester. Acetone cyanohydrin is preferably added for example in amounts of 10 mol percent.

Examples of rearrangements of benzoic esters of 5-hydroxypyrazoles are found, for example, in EP-A 282 944 or U.S. Pat. No. 4,643,757, but the only catalyst used therein is potassium carbonate or sodium carbonate in dioxane. While the use of potassium cyanide or acetone cyanohydrin has been disclosed in connection with the similar rearrangement of enol esters of cyclohexane-1,3-diones (U.S. Pat. No. 4,695,673), no examples are known from the literature for the particularly good suitability of cyanide compounds for a Fries rearrangement of O-acyl derivatives of 5-hydroxypyrazole.

Work-up is carried out in the customary manner, for example the reaction mixture is acidified with dilute mineral acids, such as 5% strength hydrochloric acid or sulfuric acid, and the mixture is extracted for example using methylene chloride or ethyl acetate. For purification, the extract is extracted using cold 5–10% strength alkali metal carbonate solution, the end product passing over into the aqueous phase. The product of the formula Ic is precipitated by acidifying the aqueous solution, or else reextracted using methylene chloride, dried and subsequently freed from the solvent.

The 5-hydroxypyrazoles of the formula II, which are used as starting material, are known and can be prepared by processes known per se (cf. EP-A 240 001 and J. Prakt. Chem. 315, 382 (1973)). 1,3-Dimethyl-5-hydroxypyrazole is a commercially available compound.

Benzoic acid derivatives of the formula III can be prepared as follows:

Benzoyl halides, such as, for example, benzoyl chlorides of the formula III (T=Cl) are prepared in a manner known per se by reacting the benzoic acids of the formula III (T=OH) with thionyl chloride. The benzoic acids of the formula III (T=OH) can be prepared in a known manner from the corresponding esters of the formula III (T=$C_1$–$C_4$-alkoxy) by means of acid or alkaline hydrolysis.

The intermediates of the formula III can be synthesized for example in accordance with diagrams 2 and 3 by the routes described hereinbelow.

Diagram 2

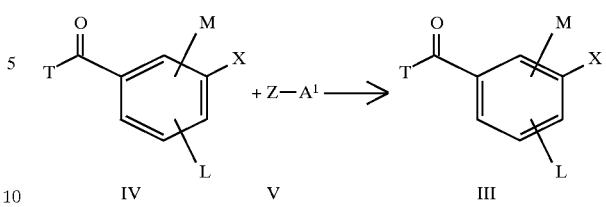

T is $C_1$–$C_4$-alkoxy,
X is Cl, Br, I, —OS(O)$_2$CF$_3$, —OS(O)$_2$F
Al is Sn($C_1$–$C_4$-alkyl)$_3$, B(OH)$_2$, ZnHal, where Hal is Cl or Br, and
L, M, Z are as defined above.

In accordance with this, the arylhalogen compounds or arylsulfonates IV can be reacted in a manner known per se with heteroaryl stannates (Stille couplings), heteroaryl boron compounds (Suzuki couplings) or heteroaryl-zinc compounds (Negishi reaction) V (cf., for example, Synthesis 1987, 51–53, Synthesis 1992, 413) in the presence of a palladium or nickel transition metal catalyst and in the presence or absence of a base to give the novel compounds of the general formula III.

The benzoic acid derivatives of the formula III can also be obtained by reacting suitable bromine- or iodine-substituted compounds of the formula VI Diagram 3

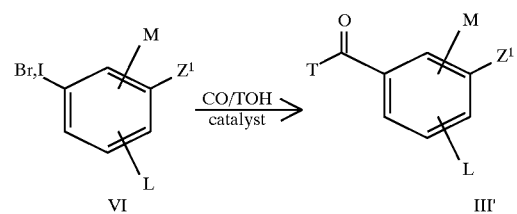

where
$Z^1$ is Z or CN,
T is OH or $C_1$–$C_4$-alkoxy and
L and M are as defined above, with carbon monoxide and water under elevated pressure in the presence of a palladium, nickel, cobalt or rhodium transition metal catalyst and of a base.

Preferred benzoyl derivatives within the scope of the present invention are those of the formula IIIa

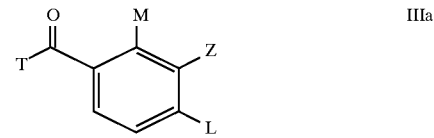

in which T, L, M and Z are as follows:
T is chlorine, OH or $C_1$–$C_4$-alkoxy,
L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano,
M is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and Z is as defined above.

Other preferred benzoyl derivatives are those of the formula IIIb

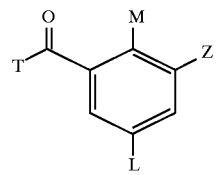

in which T, L, M and Z are as follows:

T is chlorine, OH or $C_1-C_4$-alkoxy,

L, M are $C_1-C_6$-alkyl, $C_2-C_6$-alkenyl, $C_2-C_6$-alkynyl, $C_1-C_4$-alkoxy, $C_1-C_4$-alkylthio, $C_1-C_4$-haloalkyl, $C_1-C_4$-haloalkoxy, $C_1-C_4$-haloalkylthio, $C_1-C_4$-alkylsulfonyl, halogen, nitro or cyano and Z is as defined above.

The catalysts nickel, cobalt, rhodium and, in particular, palladium, can be present in the form of metals or in the form of customary salts, such as in the form of halogen compounds, e.g. $PdCl_2$, $RhCl_3.H_2O$, acetates, e.g. $Pd(OAc)_2$, cyanides and the like, at the known valency levels. There may also exist metal complexes with tertiary phosphines, metal alkyl carbonyls, metal carbonyls, e.g. $CO_2(CO)_8$, $Ni(CO)_4$, metal carbonyl complexes with tertiary phosphines, e.g. $(PPh_3)_2Ni(CO)_2$, or transition metal salts complexed with tertiary phosphines. The lastmentioned embodiment is particularly preferred when palladium is used as the catalyst. The nature of the phosphine ligands varies widely. For example, they may be represented by the following formulae:

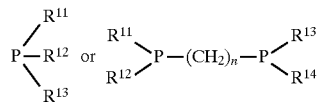

where n denotes the numbers 1, 2, 3 or 4 and the radicals $R^{11}$ to $R^{14}$ are low-molecular-weight alkyl, e.g. $C_1-C_6$-alkyl, aryl, $C_1-C_4$-alkylaryl, e.g. benzyl, phenethyl or aryloxy. Aryl is, for example, naphthyl, anthryl and, preferably, substituted or unsubstituted phenyl, where the substituents may be varied within a broad range and only their inert behavior towards the carboxylation reaction needs to be taken into account, the substituents embracing all inert C-organic radicals, such as $C_1-C_6$-alkyl radicals, e.g. methyl, carboxyl radicals, such as COOH, COOM (where M is, for example, an alkali metal, alkaline earth metal or ammonium salt), or C-organic radicals which are bonded via oxygen, such as $C_1-C_6$-alkoxy radicals.

The phosphine complexes can be prepared in a manner known per se, for example as described in the documents mentioned at the outset. For example, the starting material may be customary commercially available metal salts, such as $PdCl_2$ or $Pd(OCOCH_3)_2$, and the phosphine, e.g. $P(C_6H_5)_3$, $P(n-C_4H_9)_3$, $PCH_3(C_6H_5)_2$ or 1,2-bis(diphenylphosphino) ethane, is added.

The amount of phosphine based on the transition metal is conventionally 0 to 20, in particular 0.1 to 10, mol equivalents, particularly preferably 1 to 5 mol equivalents.

The amount of transition metal is not critical. Of course, a small amount, for example from 0.1 to 10 mol %, in particular 1 to 5 mol %, based on the starting material VI, will rather be used for financial reasons.

To prepare the benzoic acids III (T=OH), the reaction is carried out using carbon monoxide and at least equimolar amounts of water, based on the starting materials VI. The reactant water can simultaneously also act as the solvent, i.e. the maximum amount is not critical.

However, depending on the starting materials and the catalysts used, it may also be advantageous to use a different inert solvent or the base used for the carboxylation reaction as the solvent instead of the reactant.

Suitable inert solvents are solvents customary for carboxylation reactions, such as hydrocarbons, e.g. toluene, xylene, hexane, pentane, cyclohexane, ethers, e.g. methyl tert-butyl ether, tetrahydrofuran, dioxane, dimethoxyethane, substituted amides, such as dimethylformamide, persubstituted ureas, such as tetra-$C_1-C_4$-alkylureas, or nitriles such as benzonitrile or acetonitrile.

In a preferred embodiment of the process, one of the reactants, particularly the base, is used in an excess, thus dispensing with the need for an additional solvent.

Bases which are suitable for the process are all inert bases which are capable of binding the hydrogen iodide or hydrogen bromide liberated during the reaction. Examples which may be mentioned are tertiary amines, such as tert-alkylamines, e.g. trialkylamines, such as triethylamine, cyclic amines, such as N-methylpiperidine or N,N'-dimethylpiperazine, pyridine, alkali metal carbonates, alkali metal hydrogen carbonates, or tetraalkyl-substituted urea derivatives, such as tetra-$C_1-C_4$-alkylurea, for example tetramethylurea.

The amount of base is not critical, 1 to 10, in particular 1 to 5 mol, conventionally being used. If the base is simultaneously used as the solvent, the amount is, as a rule, measured in such a way that the reactants are dissolved, and unnecessarily high excesses are avoided for practical reasons, so as to save costs, to be able to use small reaction vessels and to guarantee maximum contact between the reactants.

During the reaction, the carbon monoxide pressure is adjusted in such a way that there is always an excess of CO, based on VI. The carbon monoxide pressure at room temperature is preferably 1 to 250 bar, in particular 5 to 150 bar CO.

As a rule, the carbonylation is carried out at from 20° to 250° C., in particular from 30° to 150° C., either continuously or batchwise. If the process is carried out batchwise, it is expedient to continuously inject carbon monoxide onto the reaction mixture to maintain a constant pressure.

Those arylhalogen compounds VI which are not already know can be obtained readily by a suitable combination of known syntheses.

For example, the halogen compounds VI can be obtained by Sandmeyer reaction from corresponding anilines which, in turn, can be synthesized by reducing suitable nitro compounds (cf., for example, in the case of VI where $Z^1$=CN: Liebigs Ann. Ch 1980, 768–778). The aryl bromides VI can furthermore be obtained by direct bromination of suitable starting compounds [cf., for example, Monatsh. Chem. 99, 815–822 (1968)].

Diagram 4

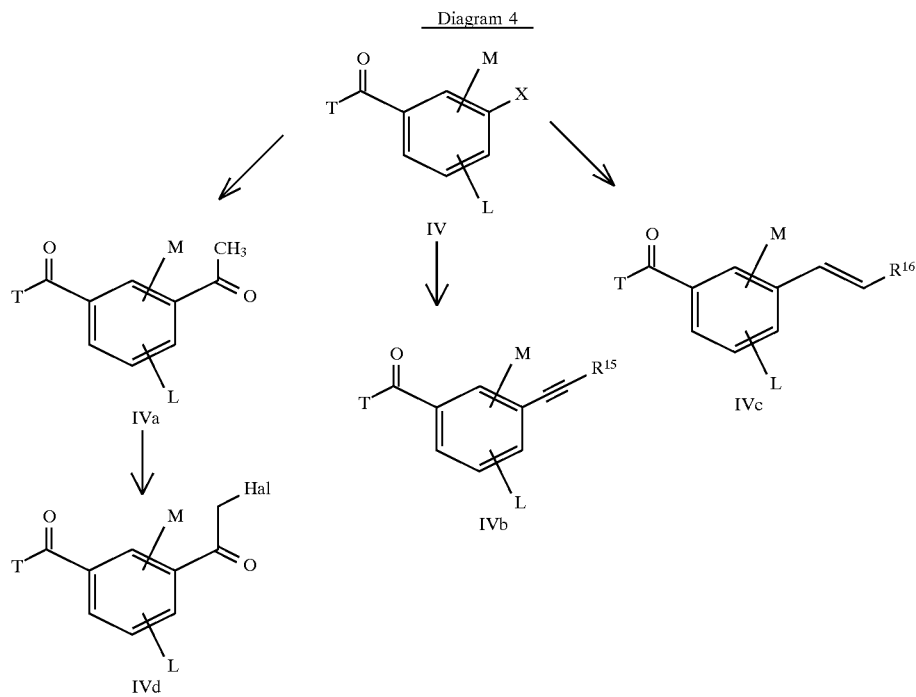

T is $C_1$–$C_4$-alkoxy,

X is Cl, Br, I, —OS(O)$_2$CF$_3$, —OS(O)$_2$F

L, M, Z are as defined above, $R^{15}$ is hydrogen, $C_1$–$C_4$-alkyl, $C_1$–$C_4$-haloalkyl, $C_3$–$C_8$-cycloalkyl, unsubstituted or substituted phenyl or trimethylsilyl, and $R^{16}$ is hydrogen, $C_1$–$C_4$-haloalkyl, $C_3$–$C_8$-cycloalkyl or unsubstituted or substituted phenyl.

In the presence of a palladium or nickel transition metal catalyst and in the presence or absence of a base, aryl methyl ketones IVa can be prepared by processes known from the literature starting from arylhalogen compounds or arylsulfonates IV by reaction with vinyl alkyl ethers, followed by hydrolysis [cf., for example, Tetrahedron Lett. 32, 1753–1756 (1991)].

The ethynylated aromatics IVb can be prepared in a manner known per se by reacting arylhalogen compounds or arylsulfonates IV with substituted acetylenes in the presence of a palladium or nickel transition metal catalyst (for example Heterocycles, 24, 31–32 (1986)). Derivatives IVb where $R^{15}$=H are expediently obtained from the silyl compounds Ivb, $R^{15}$=—Si(CH$_3$)$_3$ [J. Org. Chem. 46, 2280–2286 (1981)].

Heck reaction of arylhalogen compounds or arylsulfonates IV with olefins in the presence of a palladium catalyst gives the arylalkenes IVc (cf., for example, Heck, Palladium Reagents in Organic Synthesis, Academic Press, London 1985, or Synthesis 1993, 735–762).

Those benzoyl derivatives IV which are not already [cf., for example, Coll. Czech. Chem. Commn. 40, 3009–3019 (1975)] can be obtained in a simple manner by a suitable combination of known syntheses.

For example, the sulfonates IV (X=—OS(O)$_2$CF$_3$, —OS(O)$_2$F) can be obtained from the corresponding phenols, which in turn are known (cf., for example, EP 195247), or which can be prepared by known methods (cf., for example, Synthesis 1993, 735–762).

The halogen compounds IV (X=Cl, Br or I) can be obtained, for example, from corresponding anilines by Sandmeyer reaction.

Diagram 5

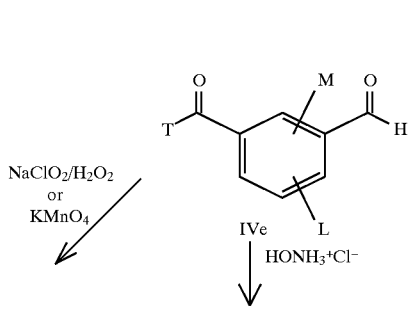

-continued
Diagram 5

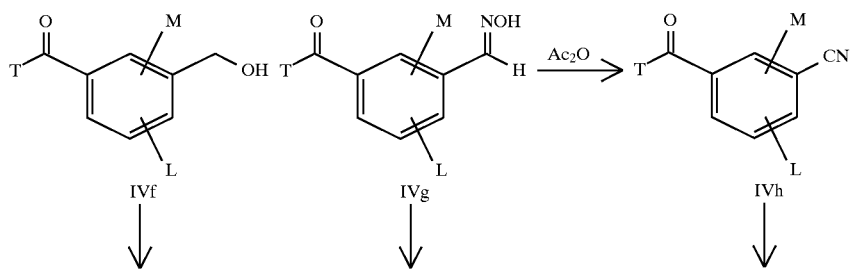

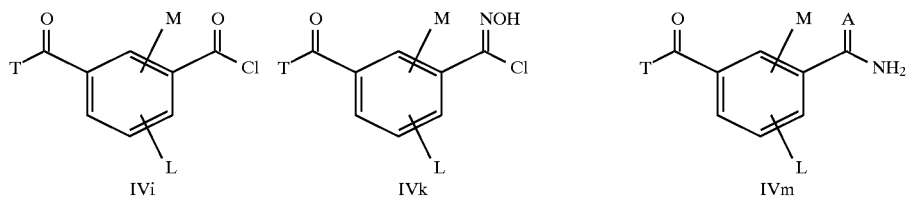

and

A is S, NH or NOH,

T is $C_1$–$C_4$-alkoxy and L and M are as defined above.

Isophthalic acid derivatives IVf can be prepared from the aldehydes IVe by known processes [see J. March Advanced Organic Chemistry 3rd Ed., p. 629 et seq., Wiley-Interscience Publication (1985)].

The oximes IVg are advantageously obtained by reacting aldehydes IVe with hydroxylamine in a manner known per se [see J. March Advanced Organic Chemistry 3rd Ed., P. 805–806, Wiley-Inter-science Publication (1985)].

The oximes IVg can be converted into nitriles IVh by processes which are also known per se [see J. March Advanced Organic Chemistry 3rd Ed., P. 931–932, Wiley-Interscience Publication (1985)].

Those aldehydes IVe which are required as starting compounds and which are not already known can be obtained by known methods. For example, they can be synthesized from the methyl compounds VII in accordance with diagram 6.

Diagram 6

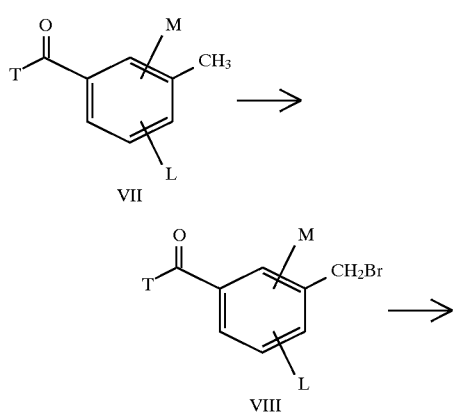

-continued
Diagram 6

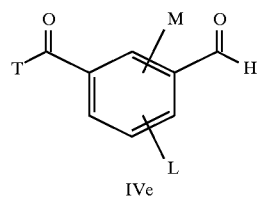

The radicals T, M and L are as defined in diagram 5. The methyl compounds VII can be reacted to give the benzyl bromides VIII by generally known methods, for example with N-bromosuccinimide or 1,3-dibromo-5,5-dimethylhydantoin. The reaction of benzyl bromides to give benzaldehydes IVe is also known from the literature [cf. Synth. Commun. 22 1967–1971 (1992)].

The precursors IVa to IVh are suitable for synthesizing heterocyclic intermediates III.

For example, 5-oxazolyl [cf., for example, J. Heterocyclic Chem., 28, 17–28 (1991)] or 4-thiazolyl derivatives [cf., for example, Metzger, Thiazoles in: The Chemistry of heterocyclic compounds, Vol.34 p. 175 et seq. (1976)] can be obtained from the acetophenones IVa via the halogenated intermediate IVd.

The acetylenes IVb or the alkenes IVc are suitable for synthesizing 4-isoxazolyl, 5-isoxazolyl, 4,5-dihydroisoxazol-4-yl, 4,5-dihydroisoxazol-5-yl derivatives [cf., for example, Houben-Weyl, Methoden der organischen Chemie [Methods in Organic Chemistry], 4th Ed., Vol. X/3, p. 843 et seq. (1965)].

2-Oxazolyl, 1,2,4-oxadiazol-5-yl or 1,3,4-oxadiazol-2-yl derivatives [cf., for example, J. Heterocyclic Chem., 28, 17–28 (1991)] or 2-pyrrolyl derivatives [cf., for example, Heterocycles 26, 3141–3151 (1987)] can be prepared, for example, by processes known from the literature from the benzoic acids IVf or from the acid chlorides IVi which can be obtained therefrom by standard methods.

1,2,4-Triazol-3-yl derivatives can be prepared from benzonitriles IVh by known methods [cf., for example, J. Chem. Soc. 3461–3464 (1954)].

The benzonitriles IVh can be converted into 1,2,4-oxadiazol-3-yl [cf., for example, J. Heterocyclic Chem., 28, 17–28 (1991)], 2-thiazolyl, 4,5-dihydrothiazol-2-yl or 5,6-dihydro-4H-1,3-thiazin-2-yl derivatives [cf., for example, Houben-Weyl, Methoden der organischen Chemie [Methods in Organic Chemistry], 4th Ed., Vol. E5, p. 1268 et seq. (1985)] via the intermediate thioamides, amidoximes or amidines IVm. In addition, 1,2,4-thiadiazol-5-yl derivatives [cf., for example, J. Org. Chem. 45 3750–3753 (1980)] or 1,3,4-thiadiazol-2-yl derivatives [cf., for example, J. Chem. Soc., Perkin Trans. I 1987–1991 (1982)] can be obtained from the thioamides IVm (A=S) by processes known from the literature.

The oximes IVg can be converted into 3-isoxazolyl derivatives in a manner known per se via the intermediate hydroxamic chlorides IVk [cf., for example, Houben-Weyl, Methoden der organischen Chemie [Methods in Organic Chemistry], 4th Ed., Vol. X/3, p. 843 et seq. (1965)].

With regard to the intended use of the benzoyl derivatives of the general formula I, the following radicals are suitable as substituents:

L and M are hydrogen, $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methyl-propyl, in particular methyl, ethyl, 1-methylethyl, 1-methylpropyl, 2-methylpropyl, 1,1-dimethylethyl and 1,l-dimethylpropyl;

$C_2$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl- 2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl, such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy, such as methoxy, ethoxy and i-propoxy, it being possible for these groups to be unsubstituted or substituted as mentioned above by one to five halogen atoms, such as fluorine, chlorine, bromine and iodine, preferably fluorine and chlorine, or $C_1$–$C_4$-alkoxy.

The group —$(Y)_n$—$S(O)_m R^7$ defined above is, for example, $C_1$–$C_4$-alkylthio, such as methylthio, ethylthio, n-propylthio, 1-methylethylthio, n-butylthio, 1-methylpropylthio, 2-methylpropylthio and 1,1-dimethylethylthio, in particular methylthio;

$C_1$–$C_4$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, in particular methylsulfinyl;

$C_1$–$C_4$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, in particular methylsulfonyl;

$C_1$–$C_4$-alkoxysulfonyl, such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl and 1,1-dimethylethoxysulfonyl, in particular methoxysulfonyl;

N-$C_1$–$C_4$-alkylsulfamoyl, such as N-methylsulfamoyl, N-ethylsulfamoyl, N-n-propylsulfamoyl, N-1-methylethylsulfamoyl, N-n-butylsulfamoyl, N-1-methylpropylsulfamoyl, N-2-methylpropylsulfamoyl and N-1,1-dimethylethylsulfamoyl, in particular N-methylsulfamoyl;

N-$C_1$–$C_4$-alkylsulfinamoyl, such as N-methylsulfinamoyl, N-ethylsulfinamoyl, N-n-propylsulfinamoyl, N-1-methylethylsulfinamoyl, N-n-butylsulfinamoyl, N-1-methylpropylsulfinamoyl, N-2-methylpropylsulfinamoyl and N-1,1-dimethylethylsulfinamoyl, in particular N-methylsulfinamoyl;

di-$C_1$–$C_4$-alkylsulfamoyl, such as dimethylsulfamoyl, diethylsulfamoyl, dipropylsulfamoyl, dibutylsulfamoyl, N-methyl-N-ethylsulfamoyl, N-methyl-N-propylsulfamoyl, N-methyl-N-1-methylethylsulfamoyl, N-methyl-N-1,1-dimethylethylsulfamoyl, di-1-methylethylsulfamoyl, N-ethyl-N-1-methylethylsulfamoyl and N-ethyl-N-1,1-dimethylethylsulfamoyl; in particular dimethylsulfamoyl;

di-$C_1$–$C_4$-alkylsulfinamoyl, such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethylethylsulfinamoyl, di-1-methylethylsulfinamoyl, N-ethyl-N-1-methylethylsulfinamoyl and N-ethyl-N-1,1-dimethylethylsulfinamoyl; in particular dimethylsulfinamoyl, $C_1$–$C_4$-alkylsulfinyloxy, such as methylsulfinyloxy, ethylsulfinyloxy, n-propylsulfinyloxy, 1-methylethylsulfinyloxy, n-butylsulfinyloxy, 1-methylpropylsulfinyloxy, 2-methylpropylsulfinyloxy and 1,1-dimethylethylsulfinyloxy, in particular methylsulfinyloxy;

$C_1$–$C_4$-alkylsulfonyloxy, such as methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy and 1,1-dimethylethylsulfonyloxy, in particular methylsulfonyloxy;

$C_1$–$C_4$-alkylsulfinylamino, such as methylsulfinylamino, ethylsulfinylamino, n-propylsulfinylamino, 1-methylethylsulfinylamino, n-butylsulfinylamino, 1-methylpropylsulfinylamino, 2-methylpropylsulfinylamino and 1,1-dimethylethylsulfinylamino, in particular methylsulfinylamino;

$C_1$–$C_4$-alkylsulfonylamino, such as methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino and 1,1-dimethylethylsulfonylamino, in particular methylsulfonylamino;

N-$C_1$–$C_4$-alkylsulfinyl-N-methylamino, such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino and N-1,1-dimethylethylsulfinyl-N-methylamino, in particular N-methylsulfinyl-N-methylamino;

N-$C_1$–$C_4$-alkylsulfinyl-N-ethylamino, such as N-methylsulfinyl-N-ethylamino, N-ethylsulfinyl-N-ethylamino, N-n-propylsulfinyl-N-ethylamino, N-1-methylethylsulfinyl-N-ethylamino, N-n-butylsulfinyl-N-ethylamino, N-1-methylpropylsulfinyl-N-ethylamino, N-2-methylpropylsulfinyl-N-ethylamino and N-1,1-dimethylethylsulfinyl-N-ethylamino, in particular N-methylsulfinyl-N-ethylamino;

N-$C_1$–$C_4$-alkylsulfonyl-N-methylamino, such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methylamino, N-1-methylpropylsulfonyl-N-methylamino, N-2-methylpropylsulfonyl-N-methylamino and N-1,1-dimethylethylsulfonyl-N-methylamino, in particular N-methylsulfonyl-N-methylamino;

N-$C_1$–$C_4$-alkylsulfonyl-N-ethylamino, such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butylsulfonyl-N-ethylamino, N-1-methylpropylsulfonyl-N-ethylamino, N-2-methylpropylsulfonyl-N-ethylamino and N-1,1-dimethylethylsulfonyl-N-ethylamino, in particular N-methylsulfonyl-N-ethylamino;

$C_1$–$C_4$-haloalkylthio, such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, in particular trifluoromethylthio.

The group —(Y)$_n$—CO—R$^8$ defined above is, for example, $C_1$–$C_4$-alkylcarbonyl, such as methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, in particular methylcarbonyl;

$C_1$–$C_4$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

N-$C_1$–$C_4$-alkylcarbamoyl, such as N-methylcarbamoyl, N-ethylcarbamoyl, N-n-propylcarbamoyl, N-1-methylethylcarbamoyl, N-n-butylcarbamoyl, N-1-methylpropylcarbamoyl, N-2-methylpropylcarbamoyl and N-1,1-dimethylethylcarbamoyl, in particular N-methylcarbamoyl;

di-$C_1$–$C_4$-alkylcarbamoyl, such as dimethylcarbamoyl, diethylcarbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, di-1-methylethylcarbamoyl, N-ethyl-N-1-methylethylcarbamoyl and N-ethyl-N-1,1-dimethylethylcarbamoyl; in particular dimethylcarbamoyl;

$C_1$–$C_4$-alkylcarbonyloxy, such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy and 1,1-dimethylethylcarbonyloxy, in particular methylcarbonyloxy;

$C_1$–$C_4$-alkylcarbonylamino, such as methylcarbonylamino, ethylcarbonylamino, n-propylcarbonylamino, 1-methylethylcarbonylamino, n-butylcarbonylamino, 1-methylpropylcarbonylamino, 2-methylpropylcarbonylamino and 1,1-dimethylethylcarbonylamino, in particular methylcarbonylamino;

N-$C_1$–$C_4$-alkylcarbonyl-N-methylamino, such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N-methylamino, N-2-methylpropylcarbonyl-N-methylamino and N-1,1-dimethylethylcarbonyl-N-methylamino, in particular N-Methylcarbonyl-N-methylamino.

Z is, for example, a saturated or unsaturated 5- or 6-membered heterocyclic radical which has one to three hetero atoms selected from the group consisting of oxygen, sulfur and nitrogen, for example a five-membered heteroaromatic radical such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 1,2,4-triazol-3-yl, 1,3,4-triazol-2-yl, 1,2,3-triazol-4-yl, 1,2,3-triazol-5-yl, 1,2,4-triazol-5-yl, tetrazol-5-yl, in particular 2-thiazolyl and 3-isoxazolyl;

a six-membered heteroaromatic radical such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-5-yl and 1,2,4-triazin-3-yl, 1,2,4-triazin-6-yl, 1,2,4,5-tetrazin-3-yl;

a saturated or partially unsaturated 5- to 6-membered heterocycle which has one to three nitrogen atoms and/or one or two oxygen or sulfur atom(s) such as 2-tetrahydrofuranyl, 3-tetrahydrofuranyl, 2-tetrahydrothienyl, 3-tetrahydrothienyl, tetrahydrothiopyran-2-yl, tetrahydrothiopyran-3-yl, tetrahydrothiopyran-4-yl, 1,3-dithiolan-2-yl, 1,3-dithiolan-4-yl, 1-3-dithian-2-yl, 1,3-dithian-4-yl, 5,6-dihydro-4H-1,3-thiazin-2-yl, 1,3-oxathiolan-2-yl, 1,3-oxathian-2-yl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 1,3-dioxolan-2-yl, 1,3-dioxolan-4-yl, 1,3-dioxan-5-yl, 1,4-dioxan-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl, in particular 2-tetrahydrofuranyl, 1,3-dioxolan-2-yl and 1,3-dioxan-2-yl, and which is unsubstituted or substituted by halogen as mentioned above, in particular fluorine or chlorine, cyano, nitro, a group —COR$^8$, for example alkylcarbonyl as mentioned above, alkoxycarbonyl as mentioneed above, N-alkylcarbamoyl as mentioned above, or dialkylcarbamoyl as mentioned above;

$C_1$–$C_4$-alkyl as mentioned above, $C_1$–$C_4$-haloalkyl such as, for example, chloromethyl, difluoromethyl, dichloromethyl, trifluoromethyl, trichloromethyl, chlorodifluoromethyl, 1-fluoroethyl, 2-fluoroethyl, 2,2-difluoroethyl, 1,1,2,2-tetrafluoroethyl, 2,2,2-trifluoroethyl, 2-chloro- 1,1,2-trifluoroethyl and pentafluoroethyl, decafluorobutyl, 1,1-bistrifluoromethyl-2,2,2-trifluoroethyl, preferably difluoromethyl, trifluoromethyl, trichloromethyl and chlorodifluoromethyl;

$C_3$–$C_8$-cycloalkyl such as, for example, cyclopropyl, cyclobutyl, cyclopentyl, cyclohexyl, cycloheptyl, cyclooctyl, in particular cyclopropyl and cyclohexyl;

$C_1$–$C_4$-alkoxy as mentioned above, $C_1$–$C_4$-haloalkoxy such as, for example, chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular $C_1$–$C_3$-haloalkoxy, such as 2,2,2-trifluoroethyloxy and 2-chloro-2,2-difluoroethoxy;

$C_1$–$C_4$-alkylthio as mentioned above, $C_1$–$C_4$-haloalkylthio as mentioned above, di-$C_1$–$C_4$-alkylamino such as, for example, dimethylamino, diethylamino, dipropylamino, dibutylamino, N-methyl-N-ethylamino, N-methyl-N-propylamino, N-methyl-N-1-methylethylamino, N-methyl-N-1,1-dimethylethylamino, di-1-methylethylamino, N-ethyl-N-1-methylethylamino and N-ethyl-N-1,1-dimethylethylamino;

substituted or unsubstituted phenyl, or an oxo group which may also be a hydroxyl group in the tautomeric form, for example thiazolin-4,5-dion-2-yl, 3-oxo-3H-1,2,4-dithiazolyl or 2-oxo-2H-1,3,4-dithiazolyl.

Benzo-fused 5- or 6-membered heteroaromatic radicals are, for example, benzofuranyl, benzothienyl, indolyl, benzoxazolyl, benzoisoxazolyl, benzothiazolyl, benzoisothiazolyl, benzopyrazolyl, indazolyl, 1,2,3-benzothiadiazolyl, 2,1,3-benzothiadiazolyl, benzotriazolyl, benzofuroxanyl, quinolinyl, isoquinolinyl, cinnolinyl, quinazolinyl, quinoxalinyl or phthalazinyl. Examples of particularly preferred compounds of the general formula I are compiled in Table 1 below.

TABLE 1

Compounds of the structure Id

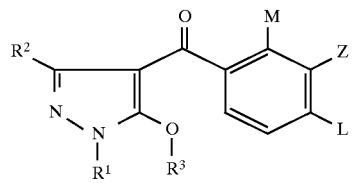

| No. | R1 | R² | R³ | L | M | Z |
|---|---|---|---|---|---|---|
| 1.1 | CH$_3$ | CH$_3$ | H | SO$_2$CH$_3$ | Cl | 2-thienyl |
| 1.2 | CH$_3$ | CH$_3$ | H | SO$_2$CH$_3$ | Cl | 3-thienyl |
| 1.3 | CH$_3$ | CH$_3$ | H | SO$_2$CH$_3$ | Cl | 2-furyl |
| 1.4 | CH$_3$ | CH$_3$ | H | SO$_2$CH$_3$ | Cl | 3-furyl |
| 1.5 | CH$_3$ | CH$_3$ | H | SO$_2$CH$_3$ | Cl | 3-methyl-isoxazol-5-yl |
| 1.6 | CH$_3$ | CH$_3$ | H | SO$_2$CH$_3$ | Cl | 5-thiazolyl |
| 1.7 | CH$_3$ | CH$_3$ | H | SO$_2$CH$_3$ | Cl | 4-thiazolyl |
| 1.8 | CH$_3$ | CH$_3$ | H | SO$_2$CH$_3$ | Cl | 2-thiazolyl |
| 1.9 | CH$_3$ | CH$_3$ | H | SO$_2$CH$_3$ | Cl | 3-methyl-isothiazol-5-yl |
| 1.10 | CH$_3$ | CH$_3$ | H | SO$_2$CH$_3$ | Cl | 3-isoxazolyl |
| 1.11 | CH$_3$ | CH$_3$ | H | SO$_2$CH$_3$ | Cl | 5-phenylthiazol-2-yl |
| 1.12 | CH$_3$ | CH$_3$ | H | SO$_2$CH$_3$ | Cl | 2-pyridyl |
| 1.13 | CH$_3$ | CH$_3$ | H | SO$_2$CH$_3$ | Cl | 3-pyridyl |
| 1.14 | CH$_3$ | CH$_3$ | H | SO$_2$CH$_3$ | Cl | 4-pyridyl |
| 1.15 | CH$_3$ | CH$_3$ | H | SO$_2$CH$_3$ | Cl | 1-methyl-2-pyrrolyl |
| 1.16 | CH$_3$ | CH$_3$ | H | SO$_2$CH$_3$ | Cl | 1-methyl-1,2,4-triazol-5-yl |
| 1.17 | CH$_3$ | CH$_3$ | H | SO$_2$CH$_3$ | Cl | 2-benzothiazolyl |
| 1.18 | CH$_3$ | CH$_3$ | H | SO$_2$CH$_3$ | Cl | 2-quinolinyl |
| 1.19 | CH$_3$ | CH$_3$ | H | SO$_2$CH$_3$ | Cl | 2-quinolinyl |
| 1.20 | CH$_3$ | CH$_3$ | H | SO$_2$CH$_3$ | Cl | 1-methylbenzimidazol-2-yl |
| 1.21 | CH$_3$ | CH$_3$ | H | SO$_2$CH$_3$ | Cl | 2-oxazolyl |
| 1.22 | CH$_3$ | CH$_3$ | H | SO$_2$CH$_3$ | Cl | 1-phenylpyrazol-5-yl |
| 1.23 | CH$_3$ | CH$_3$ | H | SO$_2$CH$_3$ | Cl | 1-methylpyrazol-3-yl |
| 1.24 | CH$_3$ | CH$_3$ | H | SO$_2$CH$_3$ | Cl | 1-methylpyrazol-5-yl |
| 1.25 | CH$_3$ | CH$_3$ | H | SO$_2$CH$_3$ | Cl | 1,3-dimethylpyrazol-3-yl |
| 1.26 | CH$_3$ | CH$_3$ | H | SO$_2$CH$_3$ | Cl | 1-phenylpyrazol-3-yl |
| 1.27 | CH$_3$ | CH$_3$ | H | SO$_2$CH$_3$ | Cl | 1,4-dimethylpyrazol-5-yl |
| 1.28 | CH$_3$ | CH$_3$ | H | SO$_2$CH$_3$ | Cl | 5-oxazolyl |
| 1.29 | CH$_3$ | CH$_3$ | H | SO$_2$CH$_3$ | Cl | 1,3-dimethylpyrazol-4-yl |
| 1.30 | CH$_3$ | CH$_3$ | H | SO$_2$CH$_3$ | Cl | 1,5-dimethylpyrazol-4-yl |
| 1.31 | CH$_3$ | CH$_3$ | H | SO$_2$CH$_3$ | Cl | 1-methylpyrazol-4-yl |
| 1.32 | CH$_3$ | CH$_3$ | H | SO$_2$CH$_3$ | Cl | 1,3-dimethylpyrazol-5-yl |
| 1.33 | CH$_3$ | CH$_3$ | H | SO$_2$CH$_3$ | Cl | 4-methyloxazol-2-yl |
| 1.34 | CH$_3$ | CH$_3$ | H | SO$_2$CH$_3$ | Cl | 5-methylthiothiazol-2-yl |

TABLE 1-continued

Compounds of the structure Id

| No. | R1 | R² | R³ | L | M | Z |
|---|---|---|---|---|---|---|
| 1.35 | CH₃ | CH₃ | H | SO₂CH₃ | Cl | 5-methylthiothiazol-2-yl |
| 1.36 | CH₃ | CH₃ | H | SO₂CH₃ | Cl | 4-methoxy-1-methyl-pyrazol-5-yl |
| 1.37 | CH₃ | CH₃ | H | SO₂CH₃ | Cl | 3-cyclopropyliso-xazol-5-yl |
| 1.38 | CH₃ | CH₃ | H | SO₂CH₃ | Cl | 3-isopropylisoxazol-5-yl |
| 1.39 | CH₃ | CH₃ | H | SO₂CH₃ | Cl | (3-methylphenyl)-thiazol-2-yl |
| 1.40 | CH₃ | CH₃ | H | SO₂CH₃ | Cl | 5-methylthiazol-2-yl |
| 1.41 | CH₃ | CH₃ | H | SO₂CH₃ | Cl | 4-bromo-2-thienyl |
| 1.42 | CH₃ | CH₃ | H | SO₂CH₃ | Cl | 5-methyl-2-thienyl |
| 1.43 | CH₃ | CH₃ | H | SO₂CH₃ | Cl | 4-methyl-2-thienyl |
| 1.44 | CH₃ | CH₃ | H | SO₂CH₃ | Cl | 4-methylthiazol-2-yl |
| 1.45 | CH₃ | CH₃ | H | SO₂CH₃ | Cl | 4-chlorothiazol-2-yl |
| 1.46 | CH₃ | CH₃ | H | SO₂CH₃ | Cl | 4,5-dimethylthiazol-2-yl |
| 1.47 | CH₃ | CH₃ | H | SO₂CH₃ | Cl | 4-phenylthiazol-2-yl |
| 1.48 | CH₃ | CH₃ | H | SO₂CH₃ | Cl | 2-methoxythiazol-5-yl |
| 1.49 | CH₃ | CH₃ | H | SO₂CH₃ | Cl | 4-methyl-2-pyridyl |
| 1.50 | CH₃ | CH₃ | H | SO₂CH₃ | Cl | 6(2-methoxyethyl)-2-pyridyl |
| 1.51 | CH₃ | CH₃ | H | SO₂CH₃ | Cl | 6-methylthio-2-pyridyl |
| 1.52 | CH₃ | CH₃ | H | SO₂CH₃ | Cl | 6-methoxy-3-pyridyl |
| 1.53 | CH₃ | CH₃ | H | SO₂CH₃ | Cl | 6-methoxy-2-pyridyl |
| 1.54 | CH₃ | CH₃ | H | SO₂CH₃ | Cl | 6-methyl-2-pyridyl |
| 1.55 | CH₃ | CH₃ | H | SO₂CH₃ | Cl | 6-(2,2,2-trifluoro-ethoxy)-2-pyridyl |
| 1.56 | CH₃ | CH₃ | H | SO₂CH₃ | Cl | 6-(2,2,2-trifluoro-ethoxy)-3-pyridyl |
| 1.57 | CH₃ | CH₃ | H | SO₂CH₃ | Cl | 5-pyrimidinyl |
| 1.58 | CH₃ | CH₃ | H | SO₂CH₃ | Cl | 6-dimethylamino-3-pyridyl |
| 1.59 | CH₃ | CH₃ | H | SO₂CH₃ | Cl | 1,2,4-thiadiazol-5-yl |
| 1.60 | CH₃ | CH₃ | H | SO₂CH₃ | Cl | 3-ethoxycarbonyl-1-methyl-pyrazol-5-yl |
| 1.61 | CH₃ | CH₃ | H | SO₂CH₃ | Cl | 2-methylthio-pyrimidin-5-yl |
| 1.62 | CH₃ | CH₃ | H | SO₂CH₃ | Cl | 2-pyrimidinyl |
| 1.63 | CH₃ | CH₃ | H | SO₂CH₃ | Cl | 2-methylthio-pyrimidin-4-yl |
| 1.64 | CH₃ | CH₃ | H | SO₂CH₃ | Cl | 5-methylthiol-1,3,4-thiadiazol-2-yl |
| 1.65 | CH₃ | CH₃ | H | SO₂CH₃ | Cl | 5-methoxy-1,3,4-thiadiazol-2-yl |
| 1.66 | CH₃ | CH₃ | H | SO₂CH₃ | Cl | 4,5-dihydrothiazol-2-yl |
| 1.67 | CH₃ | CH₃ | H | SO₂CH₃ | Cl | 5-methyloxazol-2-yl |
| 1.68 | CH₃ | CH₃ | H | SO₂CH₃ | Cl | 5-phenyloxazol-2-yl |
| 1.69 | CH₃ | CH₃ | H | SO₂CH₃ | Cl | 2-methyloxazol-5-yl |
| 1.70 | CH₃ | CH₃ | H | SO₂CH₃ | Cl | 2-phenyloxazol-5-yl |
| 1.71 | CH₃ | CH₃ | H | SO₂CH₃ | Cl | 2-methyl-1,3,4-oxadiazol-3-yl |
| 1.72 | CH₃ | CH₃ | H | SO₂CH₃ | Cl | 5-methyl-1,2,4-oxadiazol-5-yl |
| 1.73 | CH₃ | CH₃ | H | SO₂CH₃ | Cl | 2-phenyl-1,3,4-oxadiazol-5-yl |
| 1.74 | CH₃ | CH₃ | H | SO₂CH₃ | Cl | 5-trifluoromethyl-1,2,4-oxadiazol-3-yl |
| 1.75 | CH₃ | CH₃ | H | SO₂CH₃ | Cl | 5-methyl-1,2,4-oxadiazol-3-yl |
| 1.76 | CH₃ | CH₃ | H | SO₂CH₃ | Cl | 5-phenyl-1,2,4-oxadiazol-3-yl |
| 1.77 | CH₃ | CH₃ | H | SO₂CH₃ | Cl | 5-phenylisoxazol-3-yl |
| 1.78 | CH₃ | CH₃ | H | SO₂CH₃ | Cl | 1-(4-chlorophenyl)-1,2,4-triazol-2-yl |
| 1.79 | CH₃ | CH₃ | H | SO₂CH₃ | Cl | 5-cyano-4,5-dihydro-isoxyzol-3-yl |
| 1.80 | CH₃ | CH₃ | H | SO₂CH₃ | Cl | 5,6-dihydro-4H-1,3-thiazin-2-yl |
| 1.81 | CH₃ | CH₃ | H | SO₂CH₃ | Cl | 1,3-dithiolan-2-yl |
| 1.82 | CH₃ | CH₃ | H | SO₂CH₃ | Cl | 1,3-dioxolan-2-yl |
| 1.83 | CH₃ | CH₃ | H | SO₂CH₃ | Cl | 1,3-dithian-2-yl |
| 1.84 | CH₃ | CH₃ | H | SO₂CH₃ | Cl | 1,3-dioxan-2-yl |
| 1.85 | CH₃ | CH₃ | H | SO₂CH₃ | Cl | 1,3-oxathiolan-2-yl |
| 1.86 | CH₃ | CH₃ | H | SO₂CH₃ | Cl | 1,2,4-triazol-1-yl |
| 1.87 | CH₃ | CH₃ | H | SO₂CH₃ | Cl | 3-methyl-1,2,4-thiadiazol-5-yl |
| 1.88 | CH₃ | CH₃ | H | SO₂CH₃ | Cl | 1,2,4-thiadiazol-5-yl |
| 1.89 | CH₃ | CH₃ | H | SO₂CH₃ | Cl | thiazolin-4,5-dion-2-yl |
| 1.90 | CH₃ | CH₃ | H | SO₂CH₃ | Cl | 3-oxo-3-H-1,2,4-dithiazol-5-yl |
| 1.91 | CH₃ | CH₃ | H | SO₂CH₃ | Cl | 2-oxo-2-H-1,3,4-dithiazol-5-yl |
| 1.92 | CH₃ | H | H | SO₂CH₃ | Cl | 3-thienyl |
| 1.93 | CH₃ | H | H | SO₂CH₃ | Cl | 2-furyl |
| 1.94 | CH₃ | H | H | SO₂CH₃ | Cl | 3-furyl |
| 1.95 | CH₃ | H | H | SO₂CH₃ | Cl | 3-methylisoxazol-5-yl |
| 1.96 | CH₃ | H | H | SO₂CH₃ | Cl | 5-thiazolyl |
| 1.97 | CH₃ | H | H | SO₂CH₃ | Cl | 4-thiazolyl |
| 1.98 | CH₃ | H | H | SO₂CH₃ | Cl | 2-thiazolyl |
| 1.99 | CH₃ | H | H | SO₂CH₃ | Cl | 3-isoxazolyl |
| 1.100 | CH₃ | H | H | SO₂CH₃ | Cl | 2-pyridyl |
| 1.101 | CH₃ | H | H | SO₂CH₃ | Cl | 3-pyridyl |
| 1.102 | CH₃ | H | H | SO₂CH₃ | Cl | 4-pyridyl |
| 1.103 | CH₃ | H | H | SO₂CH₃ | Cl | 2-benzothiazolyl |
| 1.104 | CH₃ | H | H | SO₂CH₃ | Cl | 2-quinolinyl |
| 1.105 | CH₃ | H | H | SO₂CH₃ | Cl | 4-methyloxazol-2-yl |
| 1.106 | CH₃ | H | H | SO₂CH₃ | Cl | 5-pyrimidinyl |
| 1.107 | C₂H₅ | H | H | SO₂CH₃ | Cl | 3-thienyl |
| 1.108 | C₂H₅ | H | H | SO₂CH₃ | Cl | 2-furyl |
| 1.109 | C₂H₅ | H | H | SO₂CH₃ | Cl | 3-furyl |
| 1.110 | C₂H₅ | H | H | SO₂CH₃ | Cl | 3-methylisoxazol-5-yl |
| 1.111 | C₂H₅ | H | H | SO₂CH₃ | Cl | 5-thiazolyl |
| 1.112 | C₂H₅ | H | H | SO₂CH₃ | Cl | 4-thiazolyl |
| 1.113 | C₂H₅ | H | H | SO₂CH₃ | Cl | 2-thiazolyl |
| 1.114 | C₂H₅ | H | H | SO₂CH₃ | Cl | 3-isoxazolyl |
| 1.115 | C₂H₅ | H | H | SO₂CH₃ | Cl | 2-pyridyl |
| 1.116 | C₂H₅ | H | H | SO₂CH₃ | Cl | 3-pyridyl |
| 1.117 | C₂H₅ | H | H | SO₂CH₃ | Cl | 4-pyridyl |
| 1.118 | C₂H₅ | H | H | SO₂CH₃ | Cl | 2-benzothiazolyl |
| 1.119 | C₂H₅ | H | H | SO₂CH₃ | Cl | 2-quinolinyl |
| 1.120 | C₂H₅ | H | H | SO₂CH₃ | Cl | 4-methyloxazol-2-yl |
| 1.121 | C₂H₅ | H | H | SO₂CH₃ | Cl | 5-pyrimidinyl |
| 1.122 | C₂H₅ | H | H | SO₂CH₃ | Cl | 3-thienyl |
| 1.123 | C₂H₅ | H | H | SO₂CH₃ | Cl | 2-furyl |
| 1.124 | C₂H₅ | H | H | SO₂CH₃ | Cl | 3-furyl |
| 1.125 | C₂H₅ | H | H | SO₂CH₃ | Cl | 3-methylisoxazol-5-yl |
| 1.126 | C₂H₅ | H | H | SO₂CH₃ | Cl | 5-thiazolyl |
| 1.127 | C₂H₅ | H | H | SO₂CH₃ | Cl | 4-thiazolyl |
| 1.128 | C₂H₅ | H | H | SO₂CH₃ | Cl | 2-thiazolyl |
| 1.129 | C₂H₅ | H | H | SO₂CH₃ | Cl | 3-isoxazolyl |
| 1.130 | C₂H₅ | H | H | SO₂CH₃ | Cl | 2-pyridyl |
| 1.131 | C₂H₅ | H | H | SO₂CH₃ | Cl | 3-pyridyl |
| 1.132 | C₂H₅ | H | H | SO₂CH₃ | Cl | 4-pyridyl |
| 1.133 | C₂H₅ | H | H | SO₂CH₃ | Cl | 2-benzothiazolyl |
| 1.134 | C₂H₅ | H | H | SO₂CH₃ | Me | 2-quinolinyl |

TABLE 1-continued

Compounds of the structure Id

| No. | R1 | R² | R³ | L | M | Z |
|---|---|---|---|---|---|---|
| 1.135 | $C_2H_5$ | H | H | $SO_2CH_3$ | Me | 4-methyloxazol-2-yl |
| 1.136 | $C_2H_5$ | $CH_3$ | H | $SO_2CH_3$ | Me | 5-pyrimidinyl |
| 1.137 | $CH_3$ | $CH_3$ | H | $SO_2CH_3$ | Me | 3-thienyl |
| 1.138 | $CH_3$ | $CH_3$ | H | $SO_2CH_3$ | Me | 2-furyl |
| 1.139 | $CH_3$ | $CH_3$ | H | $SO_2CH_3$ | Me | 3-furyl |
| 1.140 | $CH_3$ | $CH_3$ | H | $SO_2CH_3$ | Me | 3-methylisoxazol-5-yl |
| 1.141 | $CH_3$ | $CH_3$ | H | $SO_2CH_3$ | Me | 5-thiazolyl |
| 1.142 | $CH_3$ | $CH_3$ | H | $SO_2CH_3$ | Me | 4-thiazolyl |
| 1.143 | $CH_3$ | $CH_3$ | R | $SO_2CH_3$ | Me | 2-thiazolyl |
| 1.144 | $CH_3$ | $CH_3$ | H | $SO_2CH_3$ | Me | 3-isoxazolyl |
| 1.145 | $CH_3$ | $CH_3$ | H | $SO_2CH_3$ | Me | 2-pyridyl |
| 1.146 | $CH_3$ | $CH_3$ | H | $SO_2CH_3$ | Me | 3-pyridyl |
| 1.147 | $CH_3$ | $CH_3$ | H | $SO_2CH_3$ | Me | 4-pyridyl |
| 1.148 | $CH_3$ | $CH_3$ | H | $SO_2CH_3$ | Me | 2-benzothiazolyl |
| 1.149 | $CH_3$ | $CH_3$ | H | $SO_2CH_3$ | $CH_3$ | 2-quinolinyl |
| 1.150 | $CH_3$ | $CH_3$ | H | $SO_2CH_3$ | $CH_3$ | 4-methyloxazol-2-yl |
| 1.151 | $CH_3$ | $CH_3$ | H | $SO_2CH_3$ | $CH_3$ | 5-pyrimidinyl |
| 1.152 | $CH_3$ | $CH_3$ | p-$CH_3$—$C_6H_4$—$SO_2$ | $SO_2CH_3$ | $CH_3$ | 3-thienyl |
| 1.153 | $CH_3$ | $CH_3$ | p-$CH_3$—$C_6H_4$—$SO_2$ | $SO_2CH_3$ | $CH_3$ | 2-furyl |
| 1.154 | $CH_3$ | $CH_3$ | p-$CH_3$—$C_6H_4$—$SO_2$ | $SO_2CH_3$ | $CH_3$ | 3-furyl |
| 1.155 | $CH_3$ | $CH_3$ | p-$CH_3$—$C_6H_4$—$SO_2$ | $SO_2CH_3$ | $CH_3$ | 3-methylisoxazol-5-yl |
| 1.156 | $CH_3$ | $CH_3$ | p-$CH_3$—$C_6H_4$—$SO_2$ | $SO_2CH_3$ | $CH_3$ | 5-thiazolyl |
| 1.157 | $CH_3$ | $CH_3$ | p-$CH_3$—$C_6H_4$—$SO_2$ | $SO_2CH_3$ | $CH_3$ | 4-thiazolyl |
| 1.158 | $CH_3$ | $CH_3$ | p-$CH_3$—$C_6H_4$—$SO_2$ | $SO_2CH_3$ | $CH_3$ | 2-thiazolyl |
| 1.159 | $CH_3$ | $CH_3$ | p-$CH_3$—$C_6H_4$—$SO_2$ | $SO_2CH_3$ | $CH_3$ | 3-isoxazolyl |
| 1.160 | $CH_3$ | $CH_3$ | p-$CH_3$—$C_6H_4$—$SO_2$ | $SO_2CH_3$ | $CH_3$ | 2-pyridyl |
| 1.161 | $CH_3$ | $CH_3$ | p-$CH_3$—$C_6H_4$—$SO_2$ | $SO_2CH_3$ | $CH_3$ | 3-pyridyl |
| 1.162 | $CH_3$ | $CH_3$ | p-$CH_3$—$C_6H_4$—$SO_2$ | $SO_2CH_3$ | $CH_3$ | 4-pyridyl |
| 1.163 | $CH_3$ | $CH_3$ | p-$CH_3$—$C_6H_4$—$SO_2$ | $SO_2CH_3$ | $CH_3$ | 2-benzothiazolyl |
| 1.164 | $CH_3$ | $CH_3$ | p-$CH_3$—$C_6H_4$—$SO_2$ | $SO_2CH_3$ | $CH_3$ | 2-quinolinyl |
| 1.165 | $CH_3$ | $CH_3$ | p-$CH_3$—$C_6H_4$—$SO_2$ | $SO_2CH_3$ | $CH_3$ | 4-methyloxazol-2-yl |
| 1.166 | $CH_3$ | $CH_3$ | p-$CH_3$—$C_6H_4$—$SO_2$ | $SO_2CH_3$ | $CH_3$ | 5-pyrimidinyl |
| 1.167 | $CH_3$ | $CF_3$ | H | $SO_2CH_3$ | Cl | 2-thienyl |
| 1.168 | $CH_3$ | $CF_3$ | H | $SO_2CH_3$ | Cl | 3-thienyl |
| 1.169 | $CH_3$ | $CF_3$ | H | $SO_2CH_3$ | Cl | 2-furyl |
| 1.170 | $CH_3$ | $CF_3$ | H | $SO_2CH_3$ | Cl | 3-furyl |
| 1.171 | $CH_3$ | $CF_3$ | H | $SO_2CH_3$ | Cl | 3-methylisoxazol-5-yl |
| 1.172 | $CH_3$ | $CF_3$ | H | $SO_2CH_3$ | Cl | 5-thiazolyl |
| 1.173 | $CH_3$ | $CF_3$ | H | $SO_2CH_3$ | Cl | 4-thiazolyl |
| 1.174 | $CH_3$ | $CF_3$ | H | $SO_2CH_3$ | Cl | 2-thiazolyl |
| 1.175 | $CH_3$ | $CF_3$ | H | $SO_2CH_3$ | Cl | 3-methylisothiazol-5-yl |
| 1.176 | $CH_3$ | $CF_3$ | H | $SO_2CH_3$ | Cl | 3-isoxazolyl |
| 1.177 | $CH_3$ | $CF_3$ | H | $SO_2CH_3$ | Cl | 5-phenylthiazol-2-yl |
| 1.178 | $CH_3$ | $CF_3$ | H | $SO_2CH_3$ | Cl | 2-pyridyl |
| 1.179 | $CH_3$ | $CF_3$ | H | $SO_2CH_3$ | Cl | 3-pyridyl |
| 1.180 | $CH_3$ | $CF_3$ | H | $SO_2CH_3$ | Cl | 4-pyridyl |
| 1.181 | $CH_3$ | $CF_3$ | H | $SO_2CH_3$ | Cl | 1-methyl-2-pyrrolyl |
| 1.182 | $CH_3$ | $CF_3$ | H | $SO_2CH_3$ | Cl | 1-methyl-1,2,4-triazol-5-yl |
| 1.183 | $CH_3$ | $CF_3$ | H | $SO_2CH_3$ | Cl | 2-benzothiazolyl |
| 1.184 | $CH_3$ | $CF_3$ | H | $SO_2CH_3$ | Cl | 2-quinolinyl |
| 1.185 | $CH_3$ | $CF_3$ | H | $SO_2CH_3$ | Cl | 2-quinolinyl |
| 1.186 | $CH_3$ | $CF_3$ | H | $SO_2CH_3$ | Cl | 1-methylbenzimidazol-2-yl |
| 1.187 | $CH_3$ | $CF_3$ | H | $SO_2CH_3$ | Cl | 2-oxazolyl |
| 1.188 | $CH_3$ | $CF_3$ | H | $SO_2CH_3$ | Cl | 5-oxazolyl |

The compounds I and their agriculturally useful salts are suitable as herbicides, both in the form of isomer mixtures and pure isomers. The herbicidal compositions comprising I control vegetation on non-cultivated land very effectively, particularly at high application rates. They act against broad-leaved weeds and grass weeds in crops such as wheat, rice, maize, soya beans and cotton without significantly damaging the crop plants. This effect is particularly pronounced at low application rates.

Taking into consideration the multiplicity of application methods, the compounds I or compositions comprising them can additionally be employed in many other crop plants for eliminating undesirable plants. Examples of suitable crops are the following:

Allium cepa, Ananas comosus, Arachis hypogaea, Asparagus officinalis, Beta vulgaris ssp. altissima, Beta vulgaris ssp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus ssp., Manihot esculenta, Medicago sativa, Musa ssp., Nicotiana tabacum (N. rustica), Olea europaea, Oryza sativa, Phaseolus lunatus, Phaseolus vulgaris, Picea abies, Pinus ssp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.

In addition, the compounds I can also be used in crops which have been made tolerant against the action of herbicides by means of breeding, including the use of genetic engineering methods.

The herbicidal compositions or the active ingredients can be applied pre- or post-emergence. If the active ingredients are less well tolerated by certain crop plants, then application techniques may be used in which the herbicidal compositions are sprayed, with the aid of the spraying equipment, in such a way that they come into as little contact as possible with the leaves of the sensitive crop plants while the active ingredients reach the leaves of undesirable plants which are growing beneath, or the naked soil surface (post-directed, lay-by).

The compounds I or the herbicidal compositions comprising them can be used, for example, in the form of ready-to-spray aqueous solutions, powders, suspensions, also highly-concentrated aqueous, oily or other suspensions or dispersions, emulsions, oil dispersions, pastes, dusts, spreading materials or granules by means of spraying, atomizing, dusting, scattering or pouring. The use forms depend on the intended purposes; in any case, they should guarantee the finest possible distribution of the active ingredients according to the invention.

Suitable inert additives are mineral oil fractions of medium to high boiling point, such as kerosene or diesel oil, furthermore coal-tar oils and oils of vegetable or animal origin, aliphatic, cyclic and aromatic hydrocarbons, e.g. paraffin, tetrahydronaphthalene, alkylated naphthalenes or derivatives thereof, alkylated benzenes or derivatives thereof, methanol, ethanol, propanol, butanol, cyclohexanol, cyclohexanone or strongly polar solvents, such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water using wetting agent, tackifier, dispersant or emulsifier. Alternatively, concentrates may be prepared which are composed of active substance, wetting agent, tackifier, dispersant or emulsifier and possibly solvent or oil, and these concentrates are suitable for dilution with water.

Suitable surface-active substances (adjuvants) are the alkali metal salts, alkaline earth metal salts or ammonium salts of aromatic sulfonic acids, e.g. ligno-, phenol-, naphthalene- and dibutylnaphthalenesulfonic acid, and of fatty acids, alkylsulfonates and alkylarylsulfonates, alkyl, lauryl ether and fatty alcohol sulfates, and salts of sulfated hexa-, hepta- and octadecanols and of fatty alcohol glycol ethers, condensation products of sulfonated naphthalene and derivatives thereof with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ethers, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignin-sulfite waste liquors or methylcellulose.

Powders, spreading materials and dusts can be prepared by mixing or grinding the active substances together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground polymers, fertilizers such as ammonium sulfate, ammonium phosphate, ammonium nitrate and ureas, plant products such as cereal meal, ground tree-bark, sawdust and ground nutshells, cellulose powder or other solid carriers.

The concentrations of the active ingredients I in the ready-to-use preparations can be varied within wide ranges. In general, the formulations comprise from 0.001 to 98% by weight, preferably 0.01 to 95% by weight, of active ingredient. The active ingredients are employed in a purity of 90% to 100%, preferably 95% to 100% (NMR spectrum).

The compounds I according to the invention can be formulated for example as follows:

20 parts by weight of the compound No. 1.28 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of the calcium salt of dodecylbenzenesulfonic acid and 5 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

20 parts by weight of the compound No. 1.28 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

20 parts by weight of the active ingredient No. 1.28 are dissolved in a mixture composed of 25 parts by weight of cyclohexanone, 65 parts by weight of a mineral oil fraction of boiling point 1.280 to 28° C. and 10 parts by weight of the adduct of 40 mol of ethylene oxide to 1 mol of castor oil.

Pouring the solution into 100,000 parts by weight of water and finely distributing it therein gives an aqueous dispersion comprising 0.02% by weight of the active ingredient.

20 parts by weight of the active ingredient No. 1.28 are mixed thoroughly with 3 parts by weight of the sodium salt of diisobutylnaphthalene-a-sulfonic acid, 17 parts by weight of the sodium salt of a lignosulfonic acid from a sulfite waste liquor and 60 parts by weight of pulverulent silica gel and the mixture is ground in a hammer mill. Fine distribution of the mixture in 20,000 parts by weight of water gives a spray mixture comprising 0.1% by weight of the active ingredient.

3 parts by weight of the active ingredient No. 1.28 are mixed with 97 parts by weight of finely divided kaolin. This gives a dust comprising 3% by weight of the active ingredient.

20 parts by weight of the active ingredient No. 1.28 are mixed intimately with 2 parts by weight of the calcium salt of dodecylbenzenesulfonic acid, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

1 part by weight of the compound No. 1.28 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

1 part by weight of the compound No. 1.28 is dissolved in a mixture composed of 80 parts by weight of cyclohexanone and 20 parts by weight of Emulphor EL. This gives a stable emulsion concentrate.

To broaden the spectrum of action and to achieve synergistic effects, the pyrazolylbenzoyl derivatives I may be mixed with a large number of representatives of other groups of herbicidal or plant-growth-regulating active ingredients and the mixtures may be applied together. Examples of suitable components for mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which have attached to them in the 2-position for example a carboxyl or carbimino group, quinolinecarboxylic acid derivatives, imidazolinones, sulfonamides, sulfonylureas, aryloxy- and heteroaryloxyphenoxypropionic acids and the salts thereof, esters and amides, as well as others.

Furthermore, it may be advantageous to apply the compounds I, alone or in combination with other herbicides, in the form of a mixture together with even more crop protection compositions, for example with compositions for controlling pests or phytopathogenic fungi or bacteria. Also of interest is the miscibility with mineral salt solutions which are employed to counteract nutritional and trace element deficiencies. It is also possible to add non-phytotoxic oils and oil concentrates.

The application rates of active ingredient are 0.001 to 3.0, preferably 0.01 to 1.0, kg/ha of active ingredient (a.i.), depending on the intended aim, the season, the target plants and the growth stage.

USE EXAMPLES

The herbicidal action of the pyrazolylbenzoyl derivatives of the formula I was demonstrated in greenhouse experiments:

The culture vessels used were plastic flowerpots containing loamy sand with approximately 3.0% humus as the substrate. The seeds of the test plants were sown separately for each species.

For the pre-emergence treatment, the active ingredients which were suspended or emulsified in water were applied directly after sowing using finely distributing nozzles. The vessels were irrigated gently to promote germination and growth and subsequently covered with translucent plastic cages until growth of the plants had started. This covering with cages causes uniform germination of the test plants, unless this was adversely affected by the active ingredients.

For the post-emergence treatment, the test plants are first grown to a height of 3 to 15 cm, depending on their growth form, and only then treated with the active ingredients which have been suspended or emulsified in water. The test plants are either sown directly and grown in the same vessels, or they are grown separately as seedlings and transplanted into the experimental vessels a few days prior to treatment.

Depending on the species, the plants were kept at 10°–25° C. or 20°–35° C. The test period was 2 to 4 weeks. During this time, the plants were tended, and their response to the individual treatments was evaluated.

Evaluation was effected using a 0 to 100 scale. 100 means no emergence of the plants or complete destruction of at least the aerial parts, while 0 means no damage, or normal growth.

TABLE 2

Herbicidal activity when used post-emergence in the greenhouse

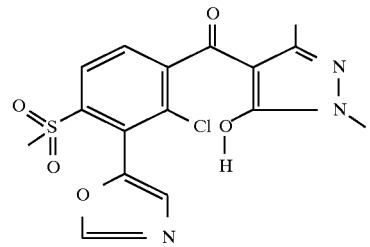

| Ex. No. | 1.28 | |
|---|---|---|
| Application rate (kg of a.i./ha) | 0.125 | 0.0625 |
| Test plants | Damage in % | |
| ZEAMX | 10 | 0 |
| CHEAL | 95 | 95 |
| SINAL | 90 | 90 |

TABLE 3

Herbicidal activity when used post-emergence in the greenhouse

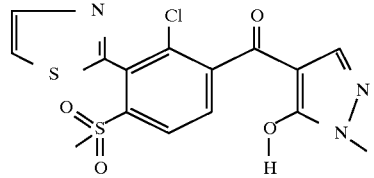

| Ex. No. | 1.98 | |
|---|---|---|
| Application rate (kg of a.i./ha) | 0.125 | 0.0625 |
| Test plants | Damage in % | |
| ZEAMX | 15 | 10 |
| ECHCG | 100 | 100 |
| SETFA | 98 | 90 |
| CHEAL | 98 | 98 |
| SINAL | 100 | 95 |

PREPARATION EXAMPLES

A) Preparation of the starting materials

1. Methyl 2-chloro-3-formyl-4-methylsulfonylbenzoate a. To a suspension of 286 g (2.14 mol) of aluminum trichloride in 420 ml of 1,2-dichloroethane there was added dropwise at 15°–20° C. a solution of 157 g (2 mol) of acetyl chloride in 420 mol of 1,2-dichloroethane. A solution of 346 g (2 mol) of 2-chloro-6-methylthiotoluene in 1 l of 1,2-dichloroethane was subsequently added dropwise. Stirring was continued for 12 hours, and the reaction mixture was poured into a mixture of 3 l of ice and 1 l of concentrated HCl. The mixture was extracted using methylene chloride, and the organic phase was washed with water, dried using sodium sulfate and concentrated. The residue was distilled in vacuo.

This gave 256 g (60% of theory) of 2-chloro-3-methyl-4-methylthioacetophenone, m.p.: 46° C.

b. 163 g (0.76 mol) of 2-chloro-3-methyl-4-methylthioacetophenone were dissolved in 1.5 l of glacial acetic acid, 18.6 g of sodium tungstate were added, and 173.3 g of 30% strength hydrogen peroxide solution were added dropwise with cooling. Stirring was continued for 2 days and the mixture was subsequently diluted with water. The solid which had precipitated was filtered off with suction, washed with water and dried.

This gave 164 g (88% of theory) of 2-chloro-3-methyl-4-methylsulfonylacetophenone, m.p.: 110°–111° C.

c. 82 g (0.33 mol) of 2-chloro-3-methyl-4-methylsulfonylacetophenone were dissolved in 700 ml of dioxane, and the solution was treated at room temperature with 1 l of a 12.5% strength sodium hypochlorite solution. Stirring was subsequently continued for 1 hour at 80° C. After cooling, two phases formed, of which the bottom phase was diluted with water and rendered weakly acidic. The solid which had precipitated was washed with water and dried.

This gave 60 g (73% of theory) of 2-chloro-3-methyl-4-methylsulfonylbenzoic acid, m.p.: 230°–231° C.

d. 100 g (0.4 mol) of 2-chloro-3-methyl-4-methylsulfonylbenzoic acid were dissolved in 1 l of methanol and HCl was passed in for 5 hours at reflux temperature. The mixture was subsequently concentrated.

This gave 88.5 g (84% of theory) of methyl 2-chloro-3-methyl-4-methylsulfonylbenzoate, m.p.: 107°–108° C.

e. 82 g (0.31 mol) of methyl 2-chloro-3-methyl-4-methylsulfonylbenzoate were dissolved in 2 l of tetrachloromethane and treated with 56 g (0.31 mol) of N-bromosuccinimide, a little at a time, with exposure to light. The reaction mixture was filtered, the filtrate concentrated and the residue taken up in 200 ml of methyl tert-butyl ether. The solution was treated with petroleum ether and the solid which had precipitated filtered off with suction and dried.

This gave 74.5 g (70% of theory) of methyl 3-bromomethyl-2-chloro-4-methylsulfonylbenzoate, m.p.: 74°–75° C.

f. A solution of 41 g (0.12 mol) of methyl 3-bromomethyl-2-chloro-4-methylsulfonylbenzoate in 250 ml of acetonitrile was treated with 42.1 g (0.36 mol) of N-methylmorpholine N-oxide. Stirring of the batch was continued for 12 hours at room temperature, followed by concentration, and the residue was taken up in ethyl acetate. The solution was extracted with water, dried using sodium sulfate and concentrated.

This gave 31.2 g (94% of theory) of methyl 2-chloro-3-formyl-4-methylsulfonylbenzoate, m.p.: 98°–105° C.

2. Methyl 2-chloro-4-methylsulfonyl-3-(trifluoromethylsulfonyl)oxybenzoate a. 101 g (0.41 mol) of 2-chloro-3-hydroxy-4-methylsulfonylbenzoic acid are dissolved in 1.3 l of methanol and HCl gas was passed in for 4 hours under reflux. The solution was concentrated, and the residue was taken up in dichloromethane and extracted using $K_2CO_3$ solution. The aqueous phase was brought to pH 7 using dilute hydrochloric acid and washed using dichloromethane. The mixture was then acidified to pH 1 and the product extracted using dichloromethane.

This gave 76.2 g (71% of theory) of methyl 2-chloro-3-hydroxy-4-methylsulfonylbenzoate.

b. A solution of 76 g (0.29 mol) of methyl 2-chloro-3-hydroxy-4-methylsulfonylbenzoate and 68 g of pyridine in 700 ml of dichloromethane was treated with 89 g (0.32 mol) of trifluoromethanesulfonic anhydride at –20° C. Stirring of the solution was continued for 12 hours at room temperature, and the solution was diluted with dichloromethane and extracted using water. The organic phase was dried over magnesium sulfate and concentrated.

This gave 94 g (82% of theory) of methyl 2-chloro-4-methylsulfonyl-3-(trifluoromethylsulfonyl)oxybenzoate, m.p.: 69° C.

B) Preparation of intermediates

1. Methyl 3-(3-isopropylisoxazol-5-yl)-4-methylsulfonylbenzoate a. 30 g (102 mmol) of methyl 3-bromo-4-methylsulfonylbenzoate, 90 mg of palladium dichloride and 240 mg of triphenylphosphine in 200 ml of diethylamine and 60 ml of dimethylformamide are treated with 10 g (102 mmol) of (trimethylsilyl)acetylene and 180 mg of copper(I) iodide, and the mixture is stirred at 40° C. for 4.5 hours. Stirring was then continued for 12 hours at room temperature. The reaction mixture was filtered, the filtrate concentrated and the residue chromatographed over silica gel using toluene as the eluent.

This gave 17.3 g (55% of theory) of methyl 4-methylsulfonyl-3-(trimethylsilyl)ethynylbenzoate as an oil.

b. 25 g of methyl 4-methylsulfonyl-3-(trimethylsilyl)ethynylbenzoate together with 100 ml of methanol and 0.9 g of potassium carbonate are stirred at room temperature for 18 hours. The solid was subsequently filtered off with suction and the filtrate concentrated and extracted using ethyl acetate/water. The organic phase was dried over sodium sulfate and concentrated.

This gave 15 g (79% of theory) of methyl 4-methylsulfonyl-3-ethynylbenzoate, m.p.: 95°–98° C.

c. 13.5 g (57 mmol) of methyl 4-methylsulfonyl-3-ethynylbenzoate are dissolved in 50 ml of dichloromethane, 5.2 g (60 mmol) of isobutyraldehyde oxime are added, and 41 g of a 12.5% strength sodium hypochlorite solution are added dropwise. Stirring of the mixture at room temperature was subsequently continued for 24 hours. The reaction batch was subsequently extracted using dichloromethane/water, the organic phase was concentrated, and the residue was chromatographed over silica gel using toluene/ethyl acetate as the eluent.

This gave 8.8 g (48% of theory) of methyl 3-(3-isopropylisoxazol-5-yl)-4-methylsulfonylbenzoate, m.p.: 102°–104° C.

2. Methyl 2-chloro-3-(isoxazol-3-yl)-4-methylsulfonylbenzoate a. 15 g (54 mmol) of methyl 2-chloro-3-formyl-4-methylsulfonylbenzoate (Ex. A.1.) and 4.2 g (60 mmol) of hydroxylamine hydrochloride are stirred with 300 ml of methanol, and a solution of 3.18 g (30 mmol) of sodium carbonate in 80 ml of water is added dropwise. The reaction mixture is stirred overnight at room temperature, the methanol is subsequently distilled off, and the batch is extracted using ether/water. The ether phase is dried using sodium sulfate and concentrated.

This gives 14.4 g (91% of theory) of methyl 2-chloro-3-hydroxyiminomethyl-4-methylsulfonylbenzoate, m.p.: 126°–128° C.

b. 5.3 g (18 mmol) of methyl 2-chloro-3-hydroxyiminomethyl-4-methylsulfonylbenzoate are dissolved in 50 ml of dichloromethane, and acetylene is passed in for 30 minutes at 0°–5° C. A spatula-tipful of sodium acetate is subsequently added, and 15 ml of a 10% strength sodium hypochlorite solution is added dropwise at 10° C. while more acetylene is passed in. After the addition has ended, acetylene is passed in at 10° C. for a further 15 minutes, and stirring is subsequently continued for 12 hours. The phases are then separated, and the organic phase is washed with water, dried using sodium sulfate and concentrated.

This gives 4.8 g (84% of theory) of methyl 2-chloro-3-(isoxazol-3-yl)-4-methylsulfonylbenzoate, m.p.: 145°–147° C.

3. Methyl 2-chloro-3-(thiazol-2-yl)-4-methylsulfonylbenzoate 33 g (88 mmol) of 2-(tributylstannyl)-thiazole, 17.5 g (44 mmol) of methyl 2-chloro-4-methylsulfonyl-3-(trifluoromethylsulfonyl)oxybenzoate (Ex. A.2.), 5.8 g of lithium chloride, 1 g of tetrakis(triphenylphosphine)palladium-(O), a spatula-tipful of 2,6-di-tert-butyl-4-methylphenol and 200 ml of 1,4-dioxane are stirred in an autoclave at 140° C. for 3 hours under inherent pressure. After cooling, the reaction mixture is filtered through a layer of silica gel, washed with methyl tert-butyl ether and concentrated. The residue is chromatographed over silica gel using toluene/ethyl acetate as the eluent.

This gives 9.1 g (62.6% of theory) of methyl 2-chloro-3-(thiazol-2-yl)-4-methylsulfonylbenzoate, m.p.: 135°–138° C.

4. Methyl 2-chloro-3-(oxazol-5-yl)-4-methylsulfonylbenzoate 25 g (0.09 mol) of methyl 2-chloro-3-formyl-4-methylsulfonylbenzoate (Ex. A.1.), 17.6 g (0.09 mol) of tosylmethylene isocyanide and 6.2 g (0.045 mol) of finely pulverulent potassium carbonate are stirred with 450 ml of methanol at reflux temperature for 5 hours. The solvent is subsequently stripped off, and the residue is taken up in ethyl acetate and extracted using water. The ethyl acetate phase is dried using sodium sulfate and concentrated.

This gives 24.7 g (87% of theory) of methyl 2-chloro-3-(oxazol-5-yl)-4-methylsulfonylbenzoate, $^1$H NMR (CDCl$_3$) δ: 8.24 (d,1H), 8.15 (s,1H), 8.01 (d,1H), 7.40 (s,1H), 4.0 (s,3H), 2.96 (s,3H)

The intermediates shown in the table which follows are obtained analogously:

TABLE 4

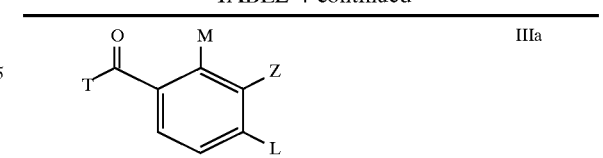

IIIa

| No. | T | L | M | Z | Physical data M.p. [°C.] or $^1$H NMR |
|---|---|---|---|---|---|
| 4.1 | methoxy | —SO$_2$Me | Cl | 3-furyl | $^1$H NMR (CDCl$_3$) δ: 8.24 (d, 1H), 7.82 (d, 1H), 7.64 (m, 2H), 6.55 (s, 1H) 3.99 (s, 3H), 2.80 (s, 3H) |
| 4.2 | methoxy | —SO$_2$Me | H | 2-thiazolyl | 95–98 |
| 4.3 | ethoxy | —SO$_2$Et | Cl | 2-thiazolyl | $^1$H NMR (CDCl$_3$) δ: 8.18 (d, 1H), 7.97 (m, 2H), 7.71 (d, 1H)), 4.47 (q, 2H) 3.36 (q, 2H), 1.42 (t, 3H), 1.24 (t, 3H) |
| 4.4 | OH | —SO$_2$CH$_3$ | Cl | 2-thiazolyl | 288–290 |
| 4.5 | OH | —SO$_2$CH$_3$ | Cl | 2-thienyl | 177–180 |
| 4.6 | OH | —SO$_2$CH$_3$ | CH$_3$ | 2-thienyl | 175–178 |
| 4.7 | OH | —SO$_2$CH$_3$ | CH$_3$ | 2-furyl | 167–171 |
| 4.8 | methoxy | —SO$_2$CH$_3$ | CH$_3$ | 2-thienyl | 91–95 |
| 4.9 | OH | —SO$_2$CH$_3$ | H | 2-furyl | 219–223 |
| 4.10 | methoxy | —SO$_2$CH$_3$ | CH$_3$ | 2-furyl | 103–106 |
| 4.11 | OH | —SO$_2$CH$_3$ | H | 2-thienyl | 222–224 |
| 4.12 | methoxy | —SO$_2$CH$_3$ | Cl | 3-isoxazolyl | $^1$H NMR (CDCl$_3$): 8.62 (1H); 8.18 (1H); 8.00 (1H); 6.58 (1H); 3.98 (3H); 3.22 (3H) |
| 4.13 | methoxy | —SO$_2$CH$_3$ | Cl | 5-phenyl-oxazol-2-yl | 115–118 |
| 4.14 | methoxy | —SO$_2$CH$_3$ | Cl | 5-oxazolyl | $^1$H NMR (CDCl$_3$): 8.76 (1H); 8.22 (1H); 8.10 (1H); 7.63 (1H); 4.04 (3H); 3.08 (3H) |
| 4.15 | methoxy | —SO$_2$CH$_3$ | Cl | 5-cyclopropyl-isoxazolyl | $^1$H NMR (CDCl$_3$): 8.20 (1H); 7.95 (1H); 6.12 (1H); 3.98 (3H); 3.22 (3H); 2.15 (1H) 1.03–1.09 (4H) |
| 4.16 | methoxy | —SO$_2$CH$_3$ | Cl | 4,5-dihydro-isoxazol-3-yl | $^1$H -NMR (CDCl$_3$): 8.12 (1H); 7.98 (1H); 4.60 (2H); 3.98 (3H); 3.42 (2H); 3.25 (3H) |
| 4.17 | methoxy | —SO$_2$CH$_3$ | Cl | 5-methyl-1,2,4-oxa-diazol-3-yl | 102–105 |
| 4.18 | methoxy | —SO$_2$CH$_3$ | Cl | 4,5-dihydro-oxazol-2-yl | $^1$H NMR (CDCl$_3$): 8.08 (1H); 7.98 (1H); 4.57 (2H); 4.12 (2H); 3.98 (3H); 3.29 (3H) |
| 4.19 | OH | —SO$_2$CH$_3$ | Cl | 3-furyl | $^1$H NMR (CDCl$_3$): 8.29 (1H); 8.02 (1H); 7.67 (2H); 6.59 (1H); 2.83 (3H) |
| 4.20 | methoxy | —SO$_2$CH$_3$ | Cl | 3-thienyl | $^1$H NMR (CDCl$_3$): 8.23 (1H); 7.84 (1H); 7.49 (2H); 7.13 (1H); 3.98 (3H); 2.62 (3H) |
| 4.21 | OH | —SO$_2$CH$_3$ | H | 3-furyl | 200–202 |
| 4.22 | OH | —SO$_2$CH$_3$ | Cl | 5-methyl-4-phenylthiazol-2-yl | 200–204 |

C) Preparation of the end products 1. 1,3-Dimethyl-4-[2-chloro-4-methylsulfonyl-3-(oxazol-5-yl)-benzoyl]-5-hydroxy-pyrazole (Example 1.28)

a. 1.22 g (10.9 mmol) of 1,3-dimethyl-5-hydroxypyrazole and 1.1 g (10.9 mmol) of triethylamine are dissolved in 75 ml of acetonitrile and treated at 0° C. with 3.5 g (10.9 mmol) of 2-chloro-4-methylsulfonyl-3-(oxazol-5-yl)-benzoyl chloride in 50 ml of acetonitrile. Stirring is continued at 0 C for 1 hour, and 4.45 g (44 mmol) of triethylamine and 0.61 g (7.2 mmol) of acetocyanohydrin are subsequently added dropwise at room temperature. The solution is stirred at room temperature for 12 hours. For working up, the mixture is first treated with dilute hydrochloric acid and extracted using methyl tert-butyl ether. The ether phase is then extracted using 5% strength potassium carbonate solution. After the aqueous phase has been acidified with hydrochloric acid, the product is extracted from the aqueous phase using ethyl acetate. The ethyl acetate phase is dried using sodium sulfate and concentrated.

This gives 1.2 g of crude product which is purified by column chromatography.

This gives 0.4 g (27% of theory) of 1,3-dimethyl-4-[2-chloro-4-methylsulfonyl-3-(oxazol-5-yl)-benzoyl]-5-hydroxy-pyrazole, m.p.: 236°–241° C.

The compound shown in the table which follows is obtained by a similar method:

TABLE 5

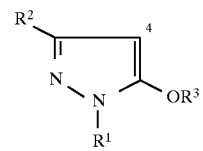

| No. | $R^1$ | $R^2$ | $R^3$ | L | M | Z | M.p. [°C.] or $^1$H NMR |
|---|---|---|---|---|---|---|---|
| 5.1. | $CH_3$ | $CF_3$ | H | $SO_2CH_3$ | Cl | 5-oxazolyl | 183–190 |
| 5.2 | $CH_3$ | $CH_3$ | H | $SO_2CH_3$ | Cl | 5-oxazolyl | 236–241 |
| 5.3 | $CH_3$ | $CH_3$ | H | $SO_2CH_3$ | Cl | 3-isoxazolyl | 117–130 |
| 5.4 | $CH_3$ | $CH_3$ | H | $SO_2CH_3$ | Cl | 4,5-dihydroisoxazol-3-yl | 125–130 |
| 5.5 | $C_2H_5$ | H | H | $SO_2CH_3$ | Cl | 4,5-dihydroisoxazol-3-yl | 61–65 |
| 5.6 | $C_2H_5$ | H | H | $SO_2CH_3$ | Cl | 3-isoxazolyl | 175–178 |
| 5.7 | $CH_3$ | $CH_3$ | H | $SO_2CH_3$ | Cl | 2-thiazolyl | 125 |
| 5.8 | $CH_3$ | $CH_3$ | H | $SO_2CH_3$ | Cl | 2-thienyl | 90 |
| 5.9 | $CH_3$ | H | H | $SO_2CH_3$ | Cl | 2-thiazolyl | 78 |
| 5.10 | $C_2H_5$ | H | H | $SO_2CH_3$ | Cl | 2-thiazolyl | 191–194 |

We claim:

1. A pyrazol-4-ylbenzoyl compound of the formula I

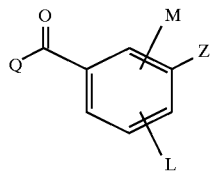

where the substituents are as follows:

L, M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy or are halogen, cyano, nitro, a group —$(Y)_n$—$S(O)_m R^7$ or a group —$(Y)_n$—CO—$R^8$ Z is a 5- or 6-membered heterocyclic saturated or unsaturated radical which has one to three hetero atoms selected from the group consisting of oxygen, sulfur and nitrogen and which is unsubstituted or substituted by halogen, cyano, nitro, a group —CO—$R^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, by phenyl which is unsubstituted or substituted by halogen, cyano, nitro, $C_1$–$C_4$-alkyl or $C_1$–$C_4$-haloalkyl, or by an oxo group which may also be present as a hydroxyl group in the tautomeric form, or which forms a bicyclic system together with a fused phenyl ring which is unsubstituted or substituted by halogen, cyano, nitro, $C_1$–$C_4$-alkyl or $C_1$–$C_4$-haloalkyl or with a fused carbocycle or with a fused second heterocycle which is unsubstituted or substituted by halogen, cyano, nitro, $C_1$–$C_4$-alkyl, di-$C_1$–$C_4$-alkylamino, $C_1$–$C_4$-alkoxy, $C_1$–$C_4$-haloalkoxy or $C_1$–$C_4$-haloalkyl, Y is O or $NR^9$, n is zero or 1, m is zero, 1 or 2, $R^7$ is $C_1$–$C_4$-alkyl, $C_1$–$C_4$-haloalkyl or $NR^9 R^{10}$ $R^8$ is $C_1$–$C_4$-alkyl, $C_1$–$C_4$-haloalkyl, $C_1$–$C_4$-alkoxy or $NR^9 R^{10}$ $R^9$ is hydrogen or $C_1$–$C_4$-alkyl, $R^{10}$ is $C_1$–$C_4$-alkyl Q is a pyrazole ring of the formula II

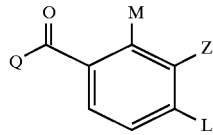

where $R^1$ is $C_1$–$C_4$-alkyl, $R^2$ is hydrogen, $C_1$–$C_4$-alkyl or $C_1$–$C_4$-haloalkyl and $R^3$ is hydrogen, $C_1$–$C_4$-alkylsulfonyl, phenylsulfonyl or alkylphenylsulfonyl and which is linked in the 4-position, or a salt of a compound I which is acceptable in agriculture.

2. A pyrazol-4-ylbenzoyl compound of the formula Ia

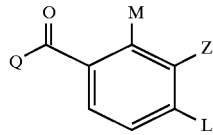

where L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and Q and Z are as defined in claim 1.

3. A pyrazol-4-ylbenzoyl compound of the formula Ib

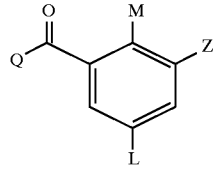

where L and M are $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and Q and Z are as defined in claim 1.

4. A pyrazol-4-ylbenzoyl compound of the formula I as defined in claim 1 where the radicals L and M are hydrogen, methyl, methoxy, methylthio, chlorine, cyano, methylsulfonyl, nitro or trifluoromethyl.

5. A process for the preparation of the pyrazol-4-ylbenzoyl compounds of the formula I as defined in claim 1, which comprises reacting the pyrazoles of the formula IIa

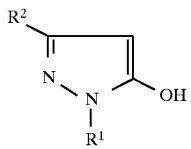

with a benzoyl compound of the formula III

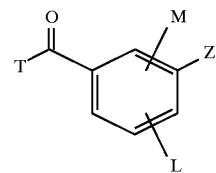

where T is halogen and L, M and Z are as defined in claim 1.

6. A herbicidal composition comprising at least one pyrazol-4-ylbenzoyl compound of the formula I as defined in claim 1 and inert additives.

7. A method of controlling undesirable vegetation, which comprises allowing a herbicidally active amount of a pyrazol-4-ylbenzoyl compound of the formula I as defined in claim 1 to act on the plants or their environment.

8. A pyrazol-4-ylbenzoyl compound of the formula I as defined in claim 1 where Z is a 5- or 6-membered heteroaromatic radical which has one to three hetero atoms selected from the group consisting of oxygen, sulfur and nitrogen and which is unsubstituted or substituted by halogen, cyano, nitro, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl which is unsubstituted or substituted by halogen, cyano, nitro, $C_1$–$C_4$-alkyl or $C_1$–$C_4$-haloalkyl, or is a 5- or 6-membered heteroaromatic ring which is benzo-fused and unsubstituted or substituted by halogen, cyano, nitro, $C_1$–$C_4$-alkyl or $C_1$–$C_4$-haloalkyl, and L, M and Q are as defined in claim 1.

* * * * *

UNITED STATES PATENT AND TRADEMARK OFFICE
CERTIFICATE OF CORRECTION

PATENT NO. : 5,846,907
DATED : December 8, 1998
INVENTOR(S) : von Deyn, et al.

It is certified that error appears in the above-identified patent and that said Letters Patent is hereby corrected as shown below:

Column 32, line 11, after "1" insert --, and subjecting the pyrazole ester formed to a rearrangement reaction in the presence of a catalyst to give the compounds of the formula 1--.

Signed and Sealed this

Sixteenth Day of March, 1999

Attest:

Q. TODD DICKINSON

Attesting Officer

Acting Commissioner of Patents and Trademarks